United States Patent [19]
Baldeschwieler et al.

[11] Patent Number: 4,915,951
[45] Date of Patent: Apr. 10, 1990

[54] CRYOPROTECTIVE REAGENT

[75] Inventors: John D. Baldeschwieler; Raymond P. Goodrich, Jr., both of Pasadena, Calif.

[73] Assignee: California Institute of Technology, Pasadena, Calif.

[21] Appl. No.: 128,152

[22] Filed: Dec. 3, 1987

[51] Int. Cl.$^4$ .................. A61K 37/22; B01J 13/02
[52] U.S. Cl. .................... 424/450; 252/407; 428/402.2; 264/4.3; 436/829
[58] Field of Search ............. 252/407; 428/402.2; 264/4.3; 424/450; 436/829

[56] References Cited

U.S. PATENT DOCUMENTS

| | | | |
|---|---|---|---|
| 4,427,649 | 1/1984 | Dingle | 424/450 |
| 4,721,612 | 1/1988 | Janoff et al. | 436/829 |
| 4,772,471 | 9/1988 | Vanlerberghe et al. | 424/450 |
| 4,804,539 | 2/1989 | Guo et al. | 424/450 |
| 4,806,343 | 2/1989 | Carpenter et al. | 424/450 |

FOREIGN PATENT DOCUMENTS

| | | | |
|---|---|---|---|
| 0009842 | 4/1980 | European Pat. Off. | 424/450 |
| 57-046921 | 3/1982 | Japan | 424/450 |

Primary Examiner—Mary C. Lee
Assistant Examiner—Catherine S. Kilby Scalzo
Attorney, Agent, or Firm—Ashen Golant Martin & Seldon

[57] ABSTRACT

Compositions for cryopreservation of phosphoglyceride-containing biological and synthetic membranes are provided in which a lipophilic anchor molecule is modified by the attachment of a preferably carbohydrate moiety placed at a predetermined, variable distance from the hydrophobic portion of the molecule by means of a hydrophilic linker unit. A method for the use of the compositions is also provided.

3 Claims, No Drawings

CRYOPROTECTIVE REAGENT

This invention was made with support from the U.S. Government through the U.S. Army Research Office under Grant number DAAG-29-83-K-0128 and also with support from the National Institute of General Medical Sciences under National Service Award T32GM07616. The U.S. Government has certain rights in the invention.

TECHNICAL FIELD

This invention relates to cryoprotection and preservation of lipid membrane structure through freezing, freeze-drying, and thawing, and in particular to stabilization of phosphoglyceride vesicle structure under such conditions.

BACKGROUND ART

Carbohydrates have demonstrated the capacity to stabilize membrane structure under the severe conditions of dehydration and freezing. This capacity has provided the opportunity to preserve biological materials in frozen or anhydrous state for prolonged periods. The amount of carbohydrate required for this effect varies, but often ranges from twenty to thirty percent (20-30%) of the sample weight. This is a significant amount; however, it is substantially lower than the amounts required of other commonly used cryoprotectants such as dimethyl sulfoxide, urea, glycerol, sucrose and ethylene glycol (Lovelock, J. E., *Biochimica et Biophysica Acta* 11, 28-36 (1979)). Additionally, use of carbohydrates avoids the deleterious effects on membrane structure which are often encountered when the other above-mentioned reagents are used.

Interest in carbohydrates as cryoprotective agents was spurred by the discovery over ten years ago that certain organisms capable of surviving in a dehydrated state for many years produced large amounts of trehalose, a non-reducing disaccharide of glucose (Madin, K. A. C., and Crowe, J. H., *Journal of Experimental Zoology*, 193, 335-342 (1975), and Loomis, S. H., O'Dell, S. J., and Crowe, J. H., *Journal of Experimental Zoology*, 211, 321-330 (1980)). Trehalose was subsequently shown to be three times more effective than sucrose and several more times effective than other cryoprotectants in preserving membrane structure and function in frozen and dehydrated systems (Crowe, L. M., Mouradian, R., Crowe, J. H., Jackson, S. A., and Womersely, C., *Biochimica et Biophysica Acta*, 769, 114-150 (1984)). It is also known that galactose can induce similar effects on membrane behavior.

All of the known cryoprotective agents are currently used in solution, to which is added the biological materials desired to be preserved. This approach requires relatively high concentrations of free carbohydrate or other agents in order to effectively reduce membrane leakage, thereby preserving the biological materials upon freezing and thawing. There has long been a need in the art for a method of treating cells, vesicles, membranes, and other biological and synthetic materials so that they may be stored in a frozen or anhydrous state for periods beyond that which is now possible.

DISCLOSURE OF INVENTION

In accordance with this invention, novel cryoprotectant compositions have been synthesized and characterized for selectively modifying a biological or synthetic phosphoglyceride membrane surface. Compositions are disclosed utilizing a lipid or lipophilic anchor such as cholesterol, suitable for intercalation into and incorporation within a phosphoglyceride bilayer, and a hydrophilic linker group of variable length, such as a hydrophilic oxyethylene unit, which is in turn attached to a polyalcohol group or a carbohydrate moiety such as maltose. The features of these novel compositions elicit significantly more pronounced effects than other agents free in the solution, require delivery of relatively small amounts of the composition, permit the incorporation of the cryoprotectant molecule into a phosphoglyceride membrane bilayer, and allow for variation in the structure, position, and mobility of the polyalcohol or carbohydrate moiety for a maximization of potential membrane interactions.

Depending on the particular application, the hydrophilic linker group may be polymerizable, the carbohydrate or other polyalcohol group provided at the end of the linker could be designed to come off at a certain time, and of course all components of the composition could be tailored for a particular purpose or impact on a membrane.

A method for use of these compositions is also provided.

The applications and methods set forth herein are merely illustrative and may be varied or modified to produce the same desirable results without departing from the scope of the inventive concept.

BEST MODES FOR CARRYING OUT THE INVENTION

As described generally above, the novel compositions of this invention contain a lipid or lipophilic anchor, which is derivatized by the attachment of a molecule with a polyhydroxyl group via a variable length hydrophilic linker.

In the presently preferred embodiment, the lipid or lipophilic anchor is cholesterol, but it could be any lipophilic molecule which may be stabilized within a biological or synthetic phosphoglyceride membrane or vesicle. Other steroids or sterols would be suitable anchors, as well as fatty acids and phospholipid derivatives.

In the presently preferred embodiment, cholesterol-p-toluenesulfonate is derivatized at the 3 position by attaching a polyoxyethylene or other hydrophilic linker unit of variable length according to methods common in the art (see, e.g., Patel, K. R., Li, M. P., Schuh, J. R., and Baldeschwieler, J. D., *Biochimica et Biophysica Acta*, 797, 20-26 (1984), and Ahmad, M. S., and Logani, S. C., *Australian Journal of Chemistry*, 24, 143-151 (1971). As Logani demonstrated, the reaction proceeds with retention of stereochemistry at the cholesterol 3 position).

Other lipophilic anchors may have different stereochemically optimum sites for derivitization. However, the determination of this site will not require undue experimentation. The presently preferred linker unit has at least two and preferably three or more oxyethylene groups (thus having a chain length of between about six and twelve angstroms), although as many as four have been found effective. Of course, other hydrophilic linker groups may be substituted, such as amine or sulfur linker groups.

In the preferred embodiment of this invention, the triethoxy derivative of cholesterol is further derivatized by the attachment of a carbohydrate at the polyethoxy linker. The synthesis utilizes a variation of the Koenigs-Knorr reaction, which reaction proceeds specifically via an acetoxonium ion to yield the 1,2-trans product (Koenigs, W. and Knorr, E., *Berichtung* 34, 957 (1901), and Six, L., Ruess, K. L., and Lieflander, M., *Tetrahedron Letters*, 24, 1229-1232 (1983)).

The presently preferred embodiment utilizes maltose as the polyhydroxyl group, but other disaccharides as well as mono- or trisaccharides could also be used. Additionally, use of a variety of compounds with polyhydroxyl groups such as inositol, dextrans and polysaccharides are envisioned in the practice of this invention.

The synthetic methodology employed for the preparation of these novel glycolipids permits variation in the structure of carbohydrate moiety, the configurations at the anomeric center of the carbohydrate, and length of the spacer unit.

These glycolipid cryoprotectants are suitable for use with biological or synthetic phosphoglyceride-containing vesicles or various cell membranes. Upon treating a cell or vesicle population with a solution containing a dispersion of the glycolipid, the glycolipid incorporates into the membrane in an appreciable amount, preferably about ten (10) to twenty (20) percent of total phosphoglyceride present. It is presently believed that percentages above this range are effective but give no significant improvement, and that below that range there is more damage to the membrane.

The stereochemical structure of the compositions of this invention as they are incorporated into a membrane is currently believed to be a significant factor in the membrane stabilization effect. It is believed that hydrogen bonding occurs between the carbohydrate moiety and the phosphoglyceride head groups so as to replace the water of hydration. This interaction is thought to increase the lateral spacing of the phosphoglyceride molecules and thus to decrease the Van der Waals interactions among the acyl chains. During conditions of freezing and/or dehydration, this effect would tend to inhibit the processes of phase transition and phase separation which produce membrane fusion and cellular damage.

As will be set forth in the examples below, cells or membranes treated in this manner may be dehydrated and subsequently rehydrated, and/or frozen and subsequently thawed without losing viability or integrity of the membrane. Intact vesicle structure after treatment has been confirmed by electron microscope (with a Phillips EM 201 microscope) $^{31}P$ NMR, light scattering, and by resonance energy transfer assay as described below.

Generally, samples are prepared in a buffered solution at pH 7.4 by brief (10-20 minute) bath sonication. The cryoprotective agent is present in this solution in prescribed ratios. Samples are frozen in liquid nitrogen ($-196°$ C.) and subsequently thawed or lyophilized under vacuum to remove water. Damage to membranes may be assessed by various conventional methods.

For treatment of cells, a dispersion of the derivatives is added to the cell suspension. The concentration of the composition will vary as described above according to amount of cells to be preserved. The suspension of the derivative is prepared by bath sonication.

INDUSTRIAL APPLICABILITY

This invention finds usefulness in a range of medical and laboratory applications. It greatly enhances current capabilities for storage of synthetic or biological materials (such as vesicles containing nutrients or any fluid, red blood cells, or any membrane-bound component) in an anhydrous and/or frozen state while preserving their functional integrity.

EXAMPLES

Example 1: Resonance Energy Transfer Assay

Methods.

In this example intermixing of treated and untreated vesicles upon freeze/thawing was examined. Cholesterol was derivatized at the 3 position with a triethoxy linker group to which was attached maltose, ("TEC-MAL"), as described above. A 0.6 to 1.2 millimolar dispersion of this derivative was applied to egg-phosphatidylcholine ("EggPC") vesicles, 5.4 mm concentration, also as described above. Some of the above EggPC:TEC-MAL vesicles contained 0.06 micromoles NBD (N-E-7-Nitro-2, 1, 3-benzoxadiazol-4-yl), a fluorescent probe ("Sample A"). Vesicles contained 0.06 micromoles Rho (rhodamine phosphatidylethanolamine), another fluorescent probe ("Sample B"), and a third group of vesicles contained both probes within the same vesicle ("Sample C"). Controls of untreated EggPC vesicles, and EggPC:TEC without carbohydrate were also prepared. All lipids were obtained from Avanti Polar Lipids, Inc., and buffer salts were purchased from Sigma and Aldrich.

Samples were prepared in a buffered solution (pH 7.4) by 10-20 minute bath sonication. Samples were dried under nitrogen and under mechanical pump vacuum for 8 hours. Each was hydrated with 0.7 ml HEPES Buffer (0.01 M HEPES, 0.12 M NaCl, pH 7.4), vortexed briefly, and probe sonicated for 15 minutes. The suspensions were spun at $12,000 \times g$ for 5 minutes to remove titanium particles and multi-lamellar vesicles.

In duplicate, 100 microliters of Sample A was mixed with 30 microliters of Sample B. A 300 microliter aliquot of this mixture was frozen in liquid nitrogen and allowed to warm up to room temperature over a period of approximately one and a half ($1\frac{1}{2}$) hours.

A calibration curve was constructed using known standards, on a SLM-4800 spectrofluorometer from SLM Aminco, using 10 microliter aliquots of sample in 2 ml buffer.

Results.

Sample C, containing both probes within the same vesicle, was considered 100 percent intermixing. The control sample of EggPC:TEC without carbohydrate gave almost 100 percent intermixing. Pure EggPC material alone resulted in 70-100 percent intermixing. In other experiments, not showed, EggPC:TEC-Galactose shows approximately $28 \pm 5.6$ percent intermixing.

One of the pooled samples had a relative intensity of approximately 0.85, and approximately 10 percent intermixing. The duplicate had a relative intensity of approximately 0.80, and about 16 percent intermixing. From the calibration chart, approximately 13 percent ($14.5 \pm 2.1$) intermixing had occurred after freeze/thawing.

These results show a minimization of lipid intermixing, and indicate a maintenance of separate vesicles. Low emission values, indicating a lot of intermixing (by fusion) and indicating damage to the membrane, were not found.

Example 2: Sizing Of Vesicles By Light Scattering

Methods.

In this example, vesicle size and shape were examined by light scattering before and after treatment with varying compounds. Egg-phosphatidylcholine vesicles were prepared as described above. Samples containing EggPC:cholesterol ("Sample A"), EggPC:TEC-Maltose ("Sample B"), EggPC ("Sample C"), EggPC:-TEC-Galactose ("Sample D") and EggPC:TEC ("Sample E") (with no terminal carbohydrate but with the linker) were prepared as in Example 1, in the mole ratios of Table I.

Samples were prepared in a buffered solution (pH 7.4) by 10-20 minute bath sonication. Samples were dried under nitrogen and under mechanical pump vacuum for 8 hours. Each was hydrated with 0.7 ml HEPES Buffer (0.01 M HEPES, 0.12 M NaCl, pH 7.4), vortexed briefly, and probe sonicated for 15 minutes (broad tip, setting High, Amplitude 1).

Samples were examined with a Malvern Light Scattering Apparatus.

Results.

Sizing of vesicles before and after treatment are documented in Table I. Increase in vesicle size indicates greater damage to the membranes and fusion.

TABLE I

| SAMPLE | MOLE RATIO | BEFORE* | AFTER* |
|---|---|---|---|
| A. EggPC:Cholesterol | 7:3 | 44.5 ± 0.7 nm | 83.0 + 1.2 nm |
| B. EggPC:TEC-Maltose | 9:1 | 26.0 ± 0.4 nm | 33 + 1.1 nm[1] |
| C. EggPC | — | 27.4 ± 0.6 nm | 59.7 + 1.2 nm |
| D. EggPC:TEC-Galactose | 9:1 | 27.3 ± 0.8 nm | 38.1 + 0.7 nm[1] |
| E. EggPC:TEC | 7:3 | 45.3 ± 0.7 nm | 600 nm[2] |

*$^Z$average values taken from analysis of correlation function.
[1]Probably indicates aggregation in sample but no significant increase in size.
[2]Possibly several rounds of fusion resulted in multilamellar vesicles.

These light scattering assays show that vesicle sizes and shapes are maintained in the presence of the compounds. Cholesterol alone, and cholesterol plus the linker are not effective.

Example 3: $^{31}$P NMR Spectroscopy.

In this example, the capacity of the glycolipid derivatives to alter the lamellar to hexagonal ($H_{II}$) phase transition in dioleoylphosphatidylethanolamine ("DOPE") was examined. Unsaturated phosphatidylethanolamines ("PE") normally undergo a lamellar to $H_{II}$ phase transition at a given temperature and pH. As is generally known in the art, the exact temperature at which this transition occurs for a particular PE type is sensitive to hydration, acyl chain composition, pH, and the presence of particular solutes. DOPE typically undergoes the lamellar to $H_{II}$ transition at approximately 10-18° C., and thus the spectra typically obtained at room temperature, in the absence of glycolipid, is characteristic of lipid organized in the $H_{II}$ phase. $^{31}$P NMR spectra of DOPE with varying glycolipids were examined.

Incorporation of cholesterol via methods set forth above into the membrane promotes formation of the hexagonal phase. In contrast, incorporation of various mole ratios to TEC and TEC-Galactose increase the temperature at which the lamellar phase exists.

Addition of 10 mole-percent TEC-Galactose results in a spectrum (not shown) with lamellar, isotropic, and hexagonal phase components. In the presence of 20 mole-percent TEC-Galactose, the phospholipid component exhibits the spectrum characteristic of a lipid in a liquid-crystalline lamellar phase. Increasing the mole ratio of glycolipid to 33 mole-percent leads to broadening of the bilayer spectrum.

The minimum concentration of the glycolipids of the present invention required to stabilize the PE membrane in a bilayer configuration is approximately 20 mole-percent. The extent of this stabilization at this mole ratio was assessed by examining the temperature-dependent behavior of the spectrum. Samples were heated from room temperature and equilibrated for 10-15 minutes prior to accumulations. Spectra were accumulated in 10 minute intervals up to 60 minutes at a fixed temperature (spectra not shown). For a DOPE:-TEC (4:1 mole ratio) mixture, DOPE begins to enter the hexagonal phase at approximately 30° C. The transition is complete by 35° C. DOPE:TEC-Galactose mixtures remain in the lamellar phase at temperatures up to 45° C. There is little variation in the spectra at this temperature for at least one hour. Heating above 45° C., however, induces the formation of hexagonal and isotropic components of the spectra. A lowering of the temperature after initial heating above 45° C. returns the spectra to that characteristic of liquid-crystalline lamellar phase pattern.

What is claimed is:

1. A composition for application to and protection of phosphoglyceride-containing biological and synthetic membranes from the disruptive effects of freezing, thawing, and freeze-drying, comprising a dispersion of molecules, each molecule consisting of a cholesterol moiety modified at the 3-position by the attachment of a carbohydrate moiety located at a predetermined, variable distance from said cholesterol moiety by means of a hydrophilic polyoxyethylene unit of predetermined variable length.

2. A composition as in claim 1, wherein said polyoxyethylene unit ranges from six to twelve angstroms in length.

3. A composition as in claim 1, wherein said carbohydrate moiety is maltose.

* * * * *